United States Patent [19]
Lee

[11] Patent Number: 5,954,737
[45] Date of Patent: Sep. 21, 1999

[54] THROMBUS MACERATOR CATHETER

[75] Inventor: Jeffrey A. Lee, Plymouth, Minn.

[73] Assignee: NeuroVasx, Inc., Plymouth, Minn.

[21] Appl. No.: 09/164,486

[22] Filed: Oct. 1, 1998

Related U.S. Application Data

[63] Continuation-in-part of application No. 60/068,189, Dec. 19, 1997.

[51] Int. Cl.$^6$ ................................................. A61M 17/00
[52] U.S. Cl. ............................................ 606/159; 606/170
[58] Field of Search .................................... 606/127, 128, 606/159, 198, 200

[56] References Cited

U.S. PATENT DOCUMENTS

| | | |
|---|---|---|
| 1,828,986 | 10/1931 | Stevens . |
| 3,495,586 | 2/1970 | Regenbogen . |
| 4,590,938 | 5/1986 | Segura et al. ............... 606/127 |
| 4,710,192 | 12/1987 | Liotta et al. . |
| 4,739,768 | 4/1988 | Engelson . |
| 4,768,505 | 9/1988 | Okada et al. ............... 606/127 |
| 4,807,626 | 2/1989 | McGirr . |
| 4,813,934 | 3/1989 | Engelson et al. . |
| 4,994,069 | 2/1991 | Ritchart et al. . |
| 5,030,201 | 7/1991 | Palestrant . |
| 5,135,494 | 8/1992 | Engelson et al. . |
| 5,184,627 | 2/1993 | de Toledo . |
| 5,284,486 | 2/1994 | Kotula et al. . |
| 5,304,195 | 4/1994 | Twyford, Jr. et al. . |
| 5,311,858 | 5/1994 | Adair . |
| 5,324,257 | 6/1994 | Osborne et al. . |
| 5,334,210 | 8/1994 | Gianturco . |
| 5,336,205 | 8/1994 | Zenzen et al. . |
| 5,370,653 | 12/1994 | Cragg . |
| 5,387,235 | 2/1995 | Chuter . |
| 5,419,774 | 5/1995 | Willard et al. . |
| 5,462,523 | 10/1995 | Samson et al. . |
| 5,490,859 | 2/1996 | Mische et al. . |
| 5,527,326 | 6/1996 | Hermann et al. . |
| 5,536,274 | 7/1996 | Neuss . |
| 5,554,114 | 9/1996 | Wallace et al. . |
| 5,569,275 | 10/1996 | Kotula et al. . |
| 5,601,539 | 2/1997 | Corso, Jr. . |
| 5,618,267 | 4/1997 | Palestrant . |

(List continued on next page.)

FOREIGN PATENT DOCUMENTS

| | | |
|---|---|---|
| 0117519 | 2/1984 | European Pat. Off. . |
| 0442137 | 12/1990 | European Pat. Off. . |
| 0737450 | 4/1996 | European Pat. Off. . |
| 0778036 | 6/1997 | European Pat. Off. . |
| 233303 | 2/1986 | Guadeloupe . |
| 9205797 | 7/1992 | Guadeloupe . |
| WO97/13455 | 4/1997 | WIPO . |
| WO97/27893 | 8/1997 | WIPO . |
| WO97/31672 | 9/1997 | WIPO . |

OTHER PUBLICATIONS

Elgiloy, "ELGILOY", *Published by Engineering Alloya Digest, Inc., Upper Montclair, New Jersey*, Printed Publication in Aug. 1963, Revised Nov. 1971, 2 pages.

Horowitz, M., et al., "Does electrothrombosis occur immediately after embolization of an aneurysm with Guglielmi detachable coils", *American Society of Neuroradiology*, AJNR, pp. 510–513, (Mar. 1997).

Singer, R.J., et al., "Covered stent Placement for Neurovascular Disease", *American Society of Neuroradiology*, AJNR, 18, pp. 507–509, (Mar. 1997).

*Primary Examiner*—Michael Buiz
*Assistant Examiner*—William W. Lewis
*Attorney, Agent, or Firm*—Schwegman, Lundberg, Woessner & Kluth, PA

[57] ABSTRACT

The present invention includes a device for macerating a thrombus in a living being. The device includes an elongated main body defining a lumen. The elongated main body includes a sleeve component, also defining the lumen, and a mandril component positioned within the sleeve lumen. The elongated main body terminates at a distal end in one or more expandable rib elements.

39 Claims, 8 Drawing Sheets

U.S. PATENT DOCUMENTS

| | | |
|---|---|---|
| 5,620,649 | 4/1997 | Trotta . |
| 5,624,396 | 4/1997 | McNamara et al. . |
| 5,626,564 | 5/1997 | Zhan et al. . |
| 5,639,277 | 6/1997 | Mariant et al. . |
| 5,643,279 | 7/1997 | Trotta . |
| 5,656,036 | 8/1997 | Palmaz . |
| 5,674,197 | 10/1997 | van Muiden et al. . |
| 5,681,335 | 10/1997 | Serra et al. . |
| 5,702,413 | 12/1997 | Lafontaine . |
| 5,782,797 | 7/1998 | Schweich, Jr. et al. . |

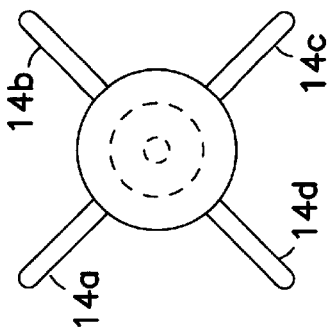
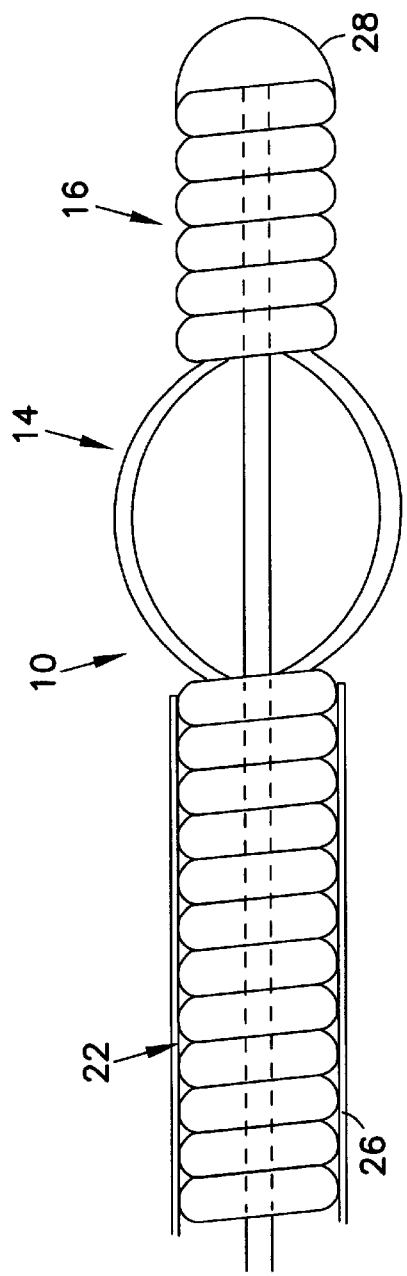

THROMBUS MACERATOR CATHETER

This Application is a Continuation-In-Part of co-pending Provisional Application 60/068,189, filed Dec. 19, 1997.

BACKGROUND OF THE INVENTION

The present invention relates to a catheter or a microcatheter for macerating a thrombus and to a method for thrombus maceration with a catheter or a micro catheter.

In an acute stroke, a blockage is formed within an artery by a thrombus or clot. One goal in treating stroke is removal of the blockage caused by the thrombus or clot as soon as possible. It is widely believed that if the blockage can be removed within the first six hours after the stroke, the chances for patient recovery with little or no neurological deficit is significantly increased. Many practitioners believe the window of opportunity is limited to the first three hours. One method of thrombus removal has included a step of dislodging the thrombus from walls of a vascular system and then removing the thrombus from the vascular system with a suction device. The Willard et al., U.S. Pat. No. 5,419,774, issuing May 30, 1995, describes a method and a device for removing a thrombus from a vascular system using this general approach. The device is used in a saphenous vein graft and is introduced without a guide wire in order to avoid a possible dislodgment of the thrombus prematurely. With this device, thrombus material is pulled into a chamber at a distal end of a catheter. The rate of pulling is regulated by pressure exerted on an irrigation solution as well as a level of vacuum pressure applied to a discharge lumen and the timing and speed of a cutter stroke.

The thrombus may also be dissolved because the thrombus is comprised of components that can be dissolved or "lysed" with drugs such as urokinase and strepto-kinase. In conventional stroke therapy these "lytic" drugs are administered via a systemic intravenous (I.V.) administration. The drugs are infused throughout the entire circulatory system so that only a very diluted concentration of drug actually contacts the thrombus.

A more aggressive treatment is to deliver the lytic drugs directly to the thrombus with a catheter. The catheter is typically positioned adjacent to the thrombus and the drugs are infused directly into the thrombus. With this form of administration, the drugs, in much higher concentrations, reach the thrombus for an improved effectiveness. However, these higher concentrations may be inadequate to dissolve a single, relatively large thrombus mass.

The Kotula et al., U.S. Pat. No. 5,569,275, issuing Oct. 29, 1996, describes a thrombus macerating device that includes an elongate, flexible shaft which can be guided along a vascular path. A rotor or impeller with blades is affixed to the shaft adjacent to its distal end. A drive mechanism is provided for rotating the shaft and the rotor which is attached to the shaft. The rotor is retained within a rotor housing and rotates within the housing. The rotor housing includes a cylindrical wall that surrounds the rotor and that has at least three ports spaced angularly about the circumference of the housing. As the rotor is rotated, it will tend to draw blood into the housing in a proximal direction and expel the blood out through the ports. The blood then tends to be drawn back into the distal end of the housing and through the rotor again. This movement sets up a recirculating vortex which repeatedly passes the blood across the blades.

When the blood is ejected through the ports in the housing within a vascular channel, the blood will act against the wall of the channel. This action maintains the housing in a position which is spaced away from the surrounding vascular wall. By spacing the ports angularly about the circumference of the housing, the force exerted by the ejected blood tends to maintain the housing and rotor carried within the housing in a position that is centered within a vascular channel.

The Kotula et al., U.S. Pat. No. 5,284,486, issuing Feb. 8, 1994, describes a mechanism for breaking down a thrombus with rotating blades. The thrombus is broken down into particles which are fine enough to be left in the vascular system without a significant risk of forming additional thrombi. The mechanism also includes another mechanism to ensure that rotating blades of the mechanism do not directly contact walls of a vessel, but remain centered within the vessel. The mechanism includes an elongate, flexible shaft with a rotor or impeller having blades affixed to the shaft adjacent its distal end. A drive mechanism is provided for rapidly rotating the shaft and the rotor attached to the shaft. The rotor is retained within a rotor housing and rotates within the housing. The rotor housing includes a generally cylindrical wall that is substantially surrounding the rotor and that has at least three ports spaced angularly about the circumference of the housing. As the rotor is rotated, it will tend to draw blood into the housing in a proximal direction and expel the blood out through the ports. The blood then tends to be drawn back into the distal end of the housing and through the rotor again. This activity sets up a recirculating vortex which repeatedly passes the blood across the blades.

SUMMARY OF THE INVENTION

The device of the present invention macerates a thrombus within a living being. The device includes an elongated main body defining a lumen. The elongated main body incudes a sleeve component defining a sleeve lumen and a mandril component positionable within the lumen of the sleeve. The elongated main body terminates at a distal end in one or more expandable rib elements.

The present invention also includes a method for macerating a thrombus within a living being. The method includes providing a device that includes a main body having a sleeve that defines a lumen and a mandril enclosable within the sleeve lumen. The mandril is adhered to the sleeve. The main body terminates in one or more ribs that are attached to an end cap. The method also includes a step of pulling the mandril so as to push the sleeve into the one or more ribs thereby decreasing a linear space that can be occupied by the ribs. As a consequence, the ribs are bowed in an outwardly direction in a balloon-shape. One other step includes positioning the device to contact a thrombus and then contacting the thrombus with the device in order to scrape the thrombus with the ribs.

BRIEF DESCRIPTION OF THE DRAWINGS

FIG. 1 illustrates a side view of one embodiment of the thrombus macerator sub-microcatheter of the present invention with a macerator component in an expanded position.

FIG. 2 illustrates an axial cross-sectional view of the macerator component of the sub-microcatheter illustrated in FIG. 1.

DETAILED DESCRIPTION OF PREFERRED EMBODIMENTS

Figure 4:
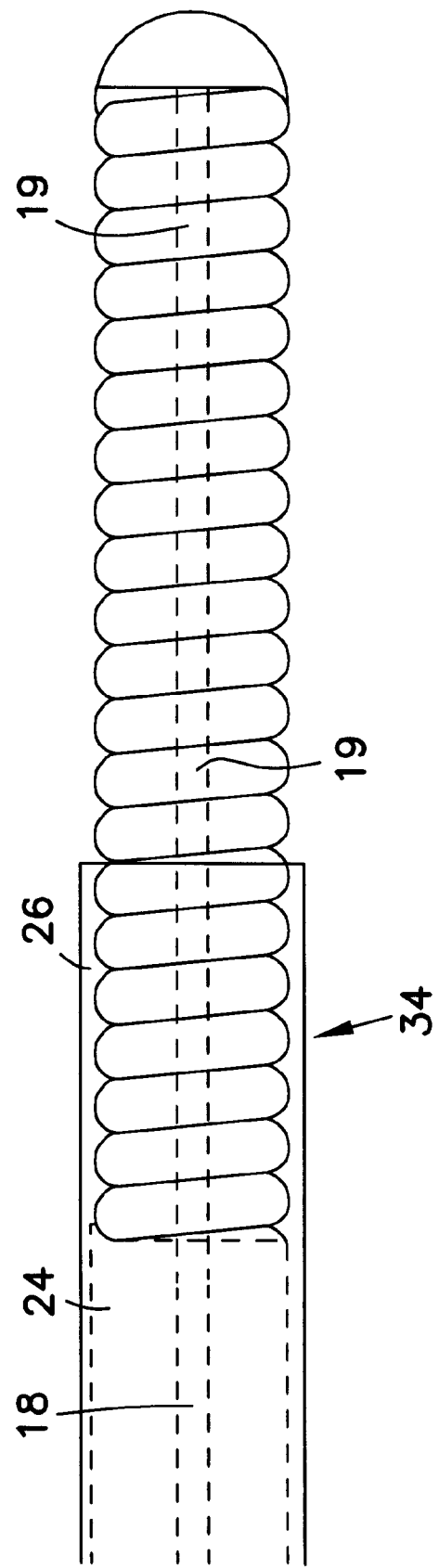
FIG. 4 illustrates one embodiment of a distal end of the thrombus macerator sub-microcatheter.

The thrombus macerating microcatheter of the present invention illustrated generally at 10 in FIG. 1 includes a tubular main body sleeve 26 with a macerator component 14 that includes a plurality of mechanically expandable ribs 14a, b, and c, shown in FIG. 2, positioned proximally to a distal end 16 of the microcatheter and a mandril 18 component positionable within a lumen 19 shown in FIG. 4 defined by the tubular main body sleeve 26 for assisting in the expansion of the mechanically expandable ribs 14. A handle 20 for manipulation of the thrombus macerator microcatheter 10 by a user is also included in the present invention. While a macerator microcatheter is described, it is understood that macerator catheters and macerator sub-microcatheters are also included in the present invention.

The thrombus macerating microcatheter 10 is typically positioned within a conventional end hole infusion catheter 22 such as is shown in FIG. 1. Specifically, the tubular main body sleeve 26 with the mechanically expandable ribs 14 at the distal end 16 is passed through a lumen of the end hole infusion catheter 22. The end hole infusion catheter is also known as an EHIC catheter. EHIC catheters are typically used for delivering lytic drugs to dissolve blood clots or thrombi. The EHIC catheter may be of varying size including a microcatheter size. Thrombi are most effectively lysed when the drug actually comes into contact with the largest possible surface area of a thrombus. It is believed that the EHIC catheter, acting in concert with the thrombus macerating microcatheter produces a synergistic effect by the combined action of local drug delivery and mechanical thrombus disruption. In particular, the expandable ribs 14 can be "raked" through a thrombus in order to break up the thrombus into smaller parts concurrently with drug delivery. These smaller thrombus parts are lysed by the local elevated concentration of lytic drugs.

The thrombus macerating microcatheter of the present invention 10 includes mechanically expandable ribs 14a, b, and c that are expandable once the microcatheter and EHIC catheter are positioned within a thrombus or blood clot, or once the macerating microcatheter 10 is expanded adjacent to the thrombus and is then advanced or retracted through the thrombus by action of the microcatheter operator, such as a physician. While the macerating microcatheter 10 is advanced or retracted through the thrombus, the ribs 14a, b, and c create abrasions or cuts within the thrombus due to movement of the ribs and the microcatheter, thereby creating an increased surface area for contact with lytic drugs. Ribs 14a, 14b, and 14c of the plurality of ribs 14 are shown in cross-section in a fully expanded position in FIG. 2. The conformation of the ribs 14a–c is changed from a linear conformation to a bowed conformation expanded or contracted by an actuating movement of the mandril 18 which acts as a rib expansion mandril. During insertion into the EHIC, the ribs 14a–c are in a contracted position to easily pass through the main body of the EHIC. The ribs 14a, b, and c may have one or more edges tapered in order to increase disruption of a thrombus by the ribs.

Figure 3A:
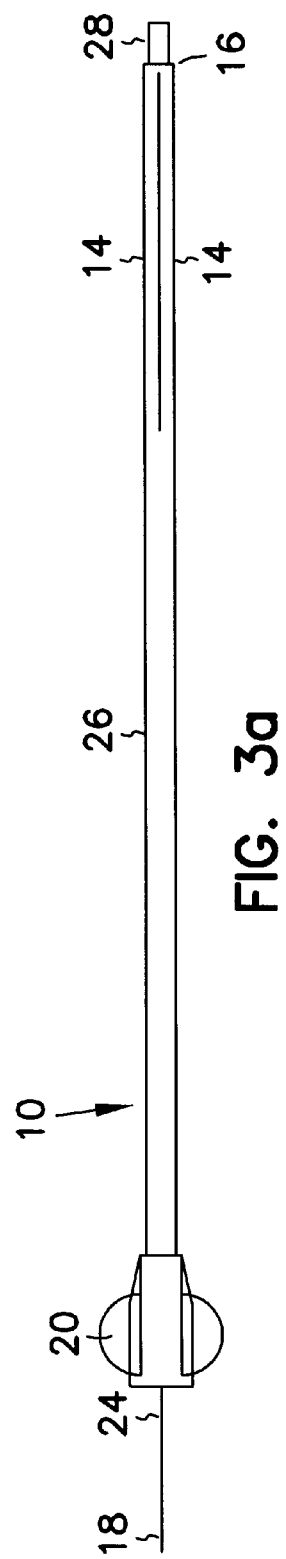
FIG. 3a illustrates the thrombus macerator sub-microcatheter of the present invention with the macerator component in an unexpanded position.

The thrombus macerating microcatheter 10 includes one embodiment of a catheter sleeve 26 illustrated in FIG. 3a, and the rib expansion mandril 18 positionable within the sleeve 26 through a lumen which is not shown. The plurality of ribs 14a–c are positioned at the distal end 16 of the microcatheter 10 and of the sleeve 26. The microcatheter 10 terminates at end 28.

Figure 3B:
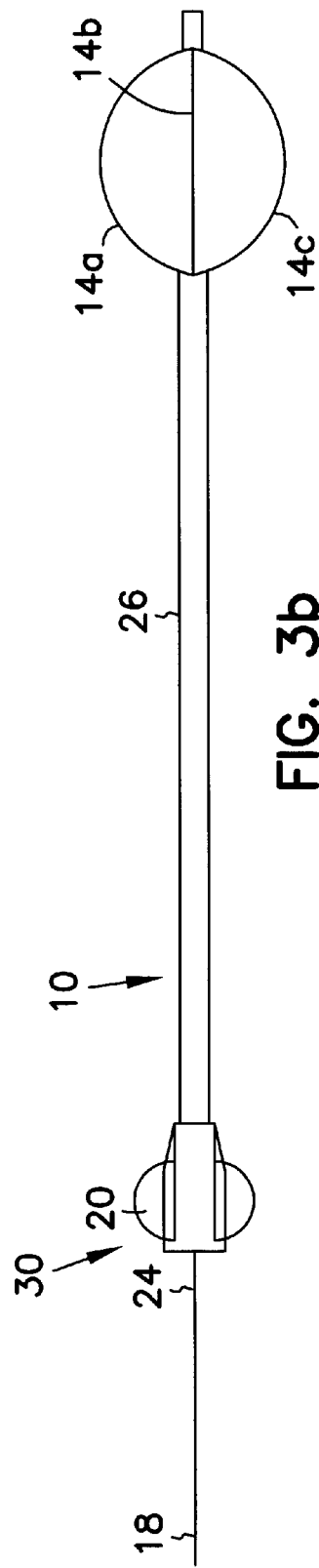
FIG. 3b illustrates the thrombus macerator sub-microcatheter with the macerator component in a fully expanded position.

The conformation of the plurality of ribs 14a, b, and c with respect to the mandril component 18 may be changed by applying a force to the mandril 18 to move the mandril 18 in a distal or proximal direction. One change in mandril 18 position and rib 14a, 14b and 14c conformation is shown between FIGS. 3b and 3b. FIG. 3b shows the mandril 18 in a first position with respect to the catheter sleeve 26 and the macerator component, i.e. the expandable ribs 14a, b, and c. When the mandril 18 is pulled by a user toward the proximal end 30 while holding the manipulation handle 20 stable, the mandril 18 is extended outwardly from a proximal end 30 of the thrombus macerating microcatheter 10. Pulling the mandril 18 effectively pushes the sleeve 26 and bows the ribs 14a, 14b and 14c of the macerator component 14. Pulling the mandril 18 while maintaining the manipulation handle 20 stable produces a movement in the distal end 28 of the microcatheter 10 without a corresponding movement of the sleeve 26. As a consequence, the linear space that can be occupied by the ribs 14a–c is decreased and the ribs 14a–c are bowed in an outwardly direction. This rib configuration is shown in FIG. 3b. As can be seen, the relative length of the macerating microcatheter 10 in FIG. 3b is less than the relative length of the microcatheter shown in FIG. 3b due to a bowing of the ribs 14a–c.

In one macerator microcatheter embodiment, the ribs of the macerator component may be preformed into a shape such as a basket shape prior to final assembly of the macerator microcatheter.

In one embodiment, the mandril 18 is attached to the sleeve 26 as shown in region 34 in FIG. 4. This fusion or bonding occurs within the bonding region 34. The region of heat fusion or adhesive bonding 34 is, in one embodiment, about 0.25 inches in length. It should be understood, however, that other dimensions may be encompassed by the present invention.

Figure 5:
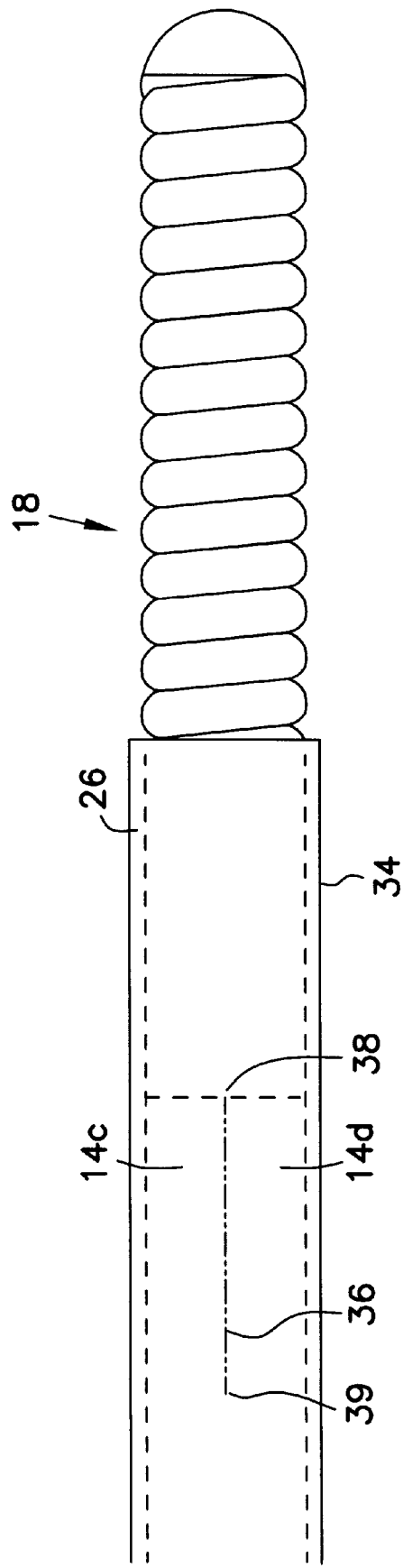
FIG. 5 illustrates a side view of the thrombus sub-microcatheter embodiment of FIG. 4.

In one embodiment illustrated in FIG. 5, the sleeve 26 defines a slit 36. The slit 36 has a first end 38 and a second end 39 proximal to the wound wire sleeve 26 and bonding region 34. The slit 36 extends along the sleeve 26, in one embodiment, for a distance of about 0.20 inches. While one slit 36 is shown in FIG. 5, it is contemplated that up to three slits be equally spaced apart along the sleeve 26 circumference to create rib 14a, 14b, and 14c.

Figure 6:
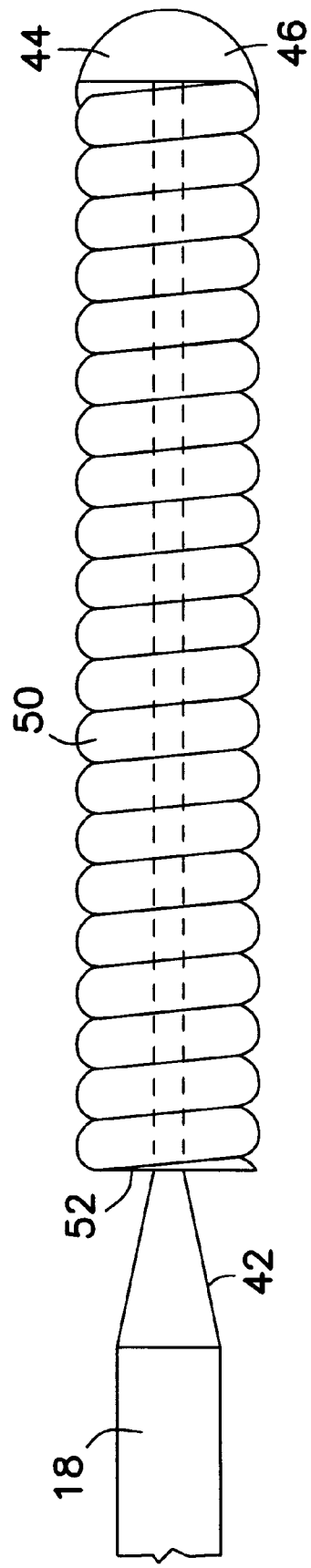
FIG. 6 illustrates a side view of a mandril positioned in the thrombus macerator sub-microcatheter shown in FIGS. 4 and 5.
Figure 7:
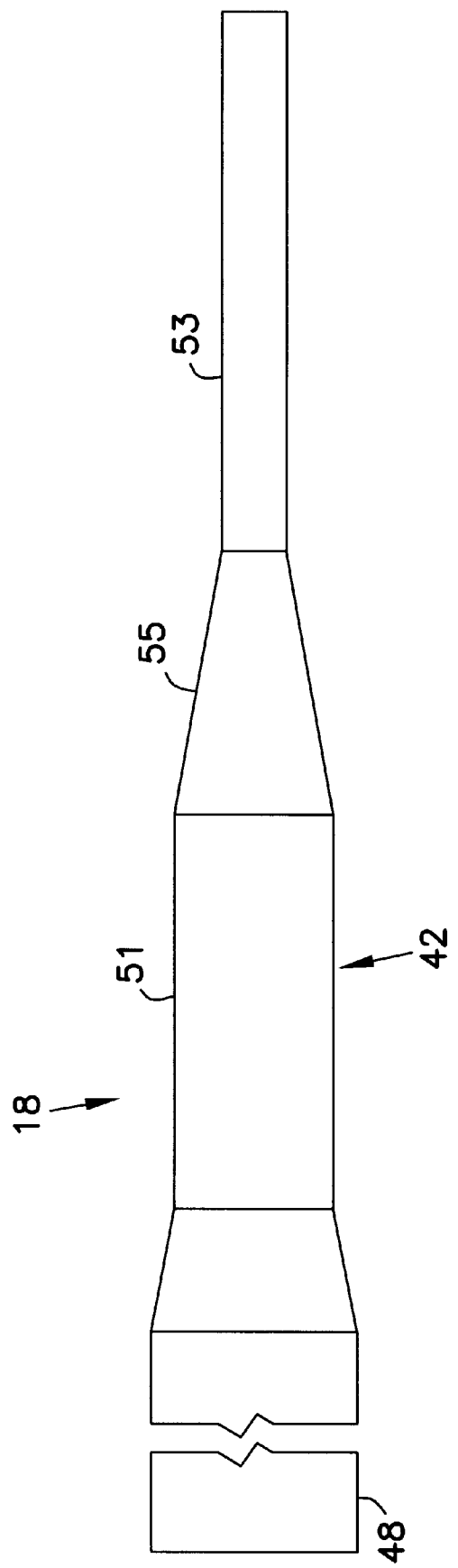
FIG. 7 is a side view of one embodiment of the mandril component for positioning in the thrombus macerator sub-microcatheter of the present invention.

One embodiment of the mandril component 18 positioned in the thrombus macerating microcatheter 10 is shown in FIGS. 6 and 7. The mandril component 18 includes an elongated main body 42 with a distal end 44 terminating in a hemispherical end cap 46 and a proximal end 48 illustrated in FIG. 7. A wound coil sleeve 50 is wound about the elongated main body 42 and terminates at the hemispherical end cap 46. The main body 42 also optionally includes a radiopaque material for monitoring the microcatheter advancement and positioning the microcatheter with fluoroscopic guidance. A proximal end 52 of the wound coil 50 is either fused or welded or otherwise permanently attached to the elongated main body 42 of the mandril 18. The end cap 46 is similarly fused or welded or otherwise permanently attached to the elongated main body 42. In one embodiment, the wound coil 50 extends along the elongated main body 42 for a distance of about 3.0 centimeters. The wound coil 50 has a maximum diameter, in one embodiment, of about 0.014 inches.

The mandril component 18 provides the flexibility and control characteristics of a steerable guidewire. The flexible wound coil 50 including the end cap 44 acts as a probing tip for advancing the microcatheter 10 through a thrombus.

This mandril embodiment illustrated in FIG. 7 is made of a super elastic Nitinol. The mandril embodiment 18 illustrated in FIG. 7 includes two elongate portions 51 and 53 conjoined by a tapered flange 55. The tubular portions 51 and 53 have different diameters. In particular, portion 53 has a smaller diameter than portion 51. The mandril 18 may be either solid Nitinol or hollow Nitinol. In one embodiment, portion 51 has a diameter of 0.008 inches and portion 53 has a diameter of 0.004 inches. Elongated portion 53 has, in one embodiment, a length of about 3.0 centimeters. The working length of the mandril is about 195 centimeters plus or minus about two centimeters. The elongated portion of the mandril 18 has a diameter of about 0.012 inches. The length of the mandril 18 from point A to point B in FIG. 7 is about 5.0 centimeters. While particular dimensions for one mandril embodiment are described, it is understood that other dimensions may be suitable for use in the macerating catheter of the present invention.

The main body of the mandril 18 provides axial rigidity that exerts and that can withstand tensile forces as well as flexural rigidity to the mandril 18 while preventing kinking and buckling and that provides torsional control for wire maneuverability. The change of distal tip diameters 42 and 44 such as is shown along the length of the mandril in FIG. 7 also provides for varying flexibility, the flexibility being greater at the distal end and less at the proximal end of the mandril 18.

A fitting assembly such as a Touhey-Borst assembly may be attached to the manipulation handle of the mandril allowing for minimal infusion of fluids or lytic drug in an annular space between the catheter sleeve inner lumen and the mandril wire. This type of control assembly provides for drug delivery through the slits in the catheter sleeve wall in order to deliver drugs into the thrombus itself when the slits are positioned within the thrombus. This type of drug delivery pre-softens the thrombus prior to maceration with the ribs 14a, 14b, 14c in an expanded position. This type of assembly also provides a fluid barrier within the catheter that prevents blood components from aggregating within the catheter itself.

The Touhey-Borst fitting also provides a locking mechanism for retaining the mandril 18 within the catheter sleeve either in a constrained state with the ribs constrained, or in a state where the ribs are expanded. This mechanism can then prevent an inadvertent expansion or contraction of the ribs.

Figure 8:
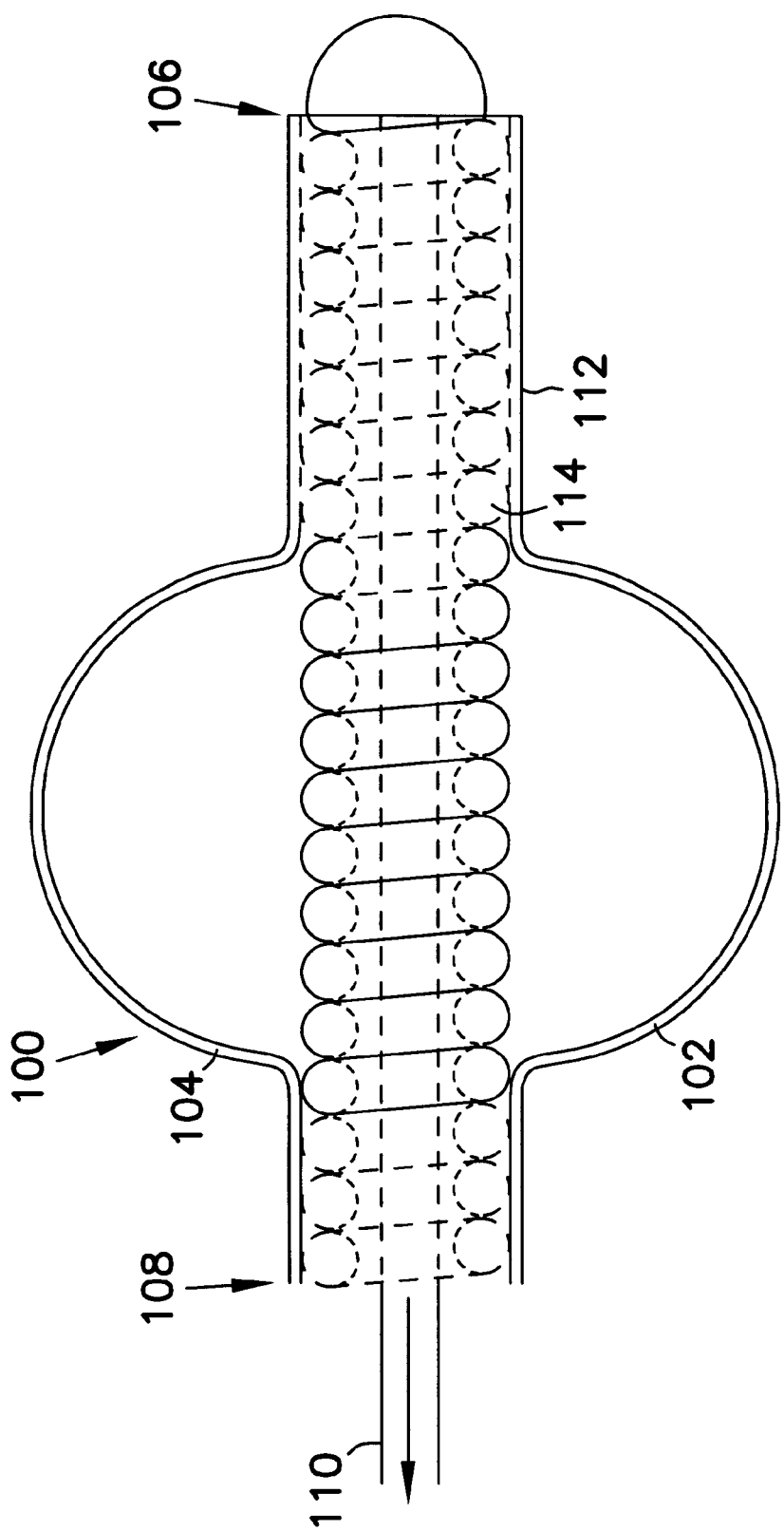
FIG. 8 is a side view of one embodiment of the thrombus macerator catheter in a position wherein macerater ribs are expanded.
Figure 9:
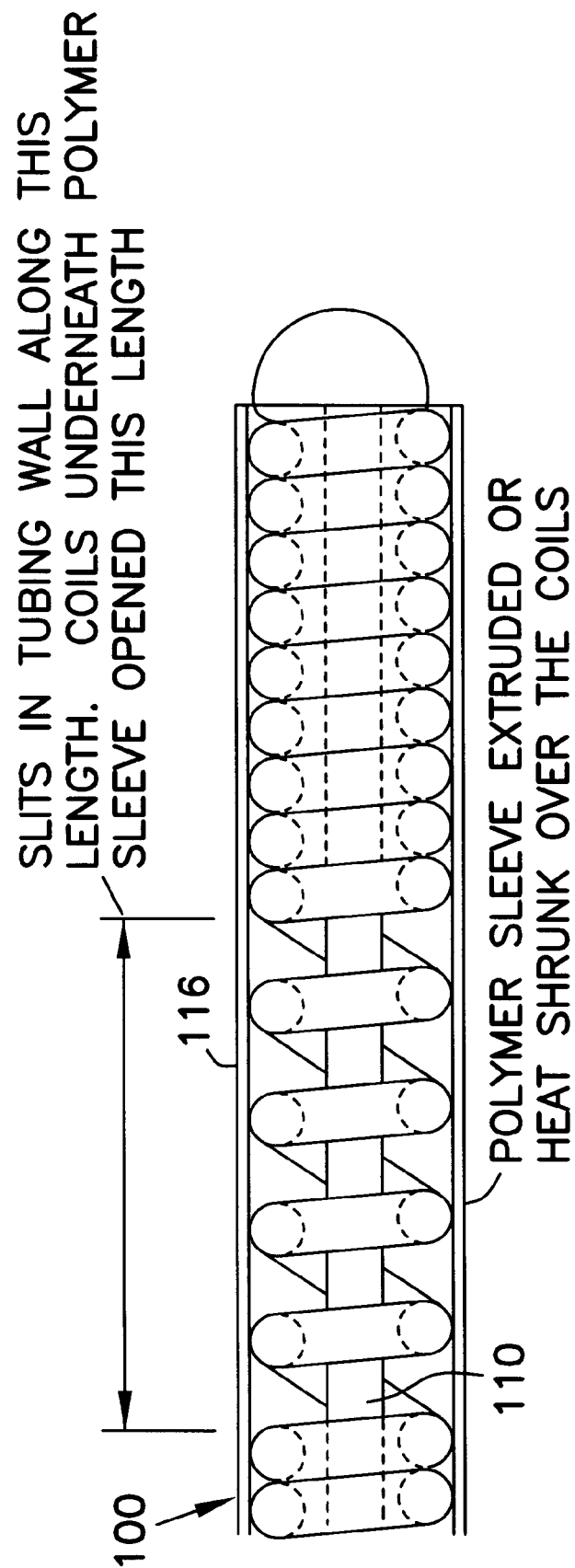
FIG. 9 is a side view of the thrombus macerater catheter of FIG. 8 wherein the macerator ribs are not expanded.

One other embodiment of the macerator microcatheter is illustrated at 100 in FIGS. 8 and 9. The macerator microcatheter 100 includes a strip 102 and a strip 104 positioned to oppose the strip 102. While a strip is described, a wire may also be used. The strips are made of a semi-rigid biocompatable material. The strips 102 and 104 terminate at each of the distal end 106 and proximal end segment 108 of the microcatheter 100. The strips 102 and 104 are adhered to the distal end 106 and proximal end segment 108 by welding or bonding or other conventionally employed adhering mechanism.

The strips 102 and 104 perform a dual function of preventing twisting of the macerator microcatheter 100 and of acting as the macerator ribs of the macerating microcatheter. It is believed that two strips provide torsional control and acceptable protection from twisting or kinking. Embodiments that include more than two strips are believed to be suitable for use in the microcatheter of the present invention.

The macerator microcatheter 100 also includes a polymer sleeve 112 and coils 114 which are substantially covered by the polymer sleeve. A core wire 110 is enclosed by the coils 114 and the sleeve 112. The polymer sleeve 112 is extruded or heat shrunk over the coils. The polymer sleeve 112 defines slits that allow the macerator strips 102 and 104 to expand or buckle. One of the slits is positioned along a length shown at 116 in FIG. 9. As the core wire 110 is retracted, the coils 114 are pulled together from an open coil orientation such as is shown in FIG. 9 to a closed coil orientation such as is shown in FIG. 8.

In order to expand or buckle the strips 102 and 104, the core wire 110 is retracted. As the core wire 110 is retracted, the coils 114 close the slits in the polymer sleeve 112. This action permits the macerator strips 102 and 104 to buckle outwardly, creating the macerator ribs.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited in the particular embodiments which have been described in detail therein. Rather, reference should be made to the appended claims as indicative of the scope and content of the present invention.

What is claimed is:

1. A device for macerating a thrombus in a living being, comprising:

an elongated main body defining a lumen that includes a sleeve component that defines two or more slits, also defining the lumen and a mandril component positioned within the sleeve lumen, the elongated main body terminating at a distal end in one or more conformable rib elements for macerating the thrombus.

2. The device of claim 1 wherein the number of conformable rib elements is two.

3. The device of claim 1 wherein the mandril is positioned at least partially within a sheath.

4. The device of claim 1 and further comprising a wire coil positioned about the elongated main body.

5. The device of claim 4 wherein the mandril is positioned at least partially within a the wire coil.

6. The device of claim 1 wherein the mandril is made of Nitinol.

7. The device of claim 1 wherein an application of a directed force on the mandril produces movement of the sleeve component toward the conformable rib element and bows the conformable rib element.

8. The device of claim 1 wherein an application of a directed force on the mandril produces movement of the sleeve component away from the conformable rib element and conforms the conformable rib element to a linear shape.

9. The device of claim 1 wherein the mandril and the sleeve component form an annulus within the elongated main body.

10. The device of claim 1 and further comprising drugs which are added to the device and released through the slit.

11. The device of claim 1 wherein the mandril component is attached to the sleeve component.

12. The device of claim 1 wherein the sleeve component and mandril component define an annular space.

13. A device for macerating a thrombus in a living being, comprising:
an elongated main body defining a lumen that includes a sleeve component, also defining the lumen and a mandril component positioned within the sleeve component wherein the sleeve component is adhered to the mandril component, the elongated main body terminating at a distal end in one or more conformable rib elements for macerating the thrombus.

14. The device of claim 13 wherein the number of conformable rib elements is two.

15. The device of claim 13 wherein the mandril is positioned at least partially within a sheath.

16. The device of claim 13 wherein the sleeve component defines two or more slits.

17. The device of claim 13 wherein the mandril is made of Nitinol.

18. A device for macerating a thrombus in a living being, comprising:
an elongated main body with a distal end and a proximal end that terminates at the distal end to a flexible guidewire, the main body defining a lumen that includes a sleeve component also defining the lumen and a mandril component positioned within the sleeve lumen, the elongated main body terminating at a distal end in one or more conformable rib elements for macerating the thrombus.

19. The device of claim 18 wherein the number of rib elements is two.

20. The device of claim 18 wherein the sleeve defines two or more slits.

21. The device of claim 18 wherein the sleeve is adhered to the mandril component.

22. The device of claim 18 wherein the mandril component is positioned at least partially within a sheath.

23. The device of claim 18 wherein the mandril component is positioned at least partially within a wire coil.

24. The device of claim 18 wherein the mandril component is made of Nitinol.

25. The device of claim 18 wherein an application of a directed force on the mandril component produces movement of the sleeve component away from the ribs and conforms the conformable rib elements to a linear shape.

26. The device of claim 18 wherein an application of a directed force on the mandril component produces movement of the sleeve component toward the ribs and bows the ribs.

27. The device of claim 18 wherein the mandril component is attached to the sleeve component.

28. The device of claim 18 wherein the sleeve component and mandril component define an annular space.

29. A device for macerating a thrombus in a living being, comprising: an elongated main body defining a lumen that includes a sleeve component also defining the lumen and a mandril component positioned within the sleeve lumen, the elongated main body terminating at a distal end in one or more conformable rib elements for macerating the thrombus and further including one or more strip components positioned over the sleeve component and terminating at the distal end and at a proximal end segment.

30. The device of claim 20 wherein the strip component prevents twisting of the device and functions as a macerating rib.

31. A method for macerating a thrombus in a living being, comprising:
providing a device that includes a main body that includes a sleeve defining a lumen and a mandril enclosed within the sleeve and adhered to the sleeve, the main body terminating in one or more ribs attached to an end cap;

pulling the mandril so as to push the sleeve into the ribs thereby decreasing a linear space that can be occupied by the ribs thereby bowing the ribs in an outwardly direction;

positioning the device to contact a thrombus and contacting the thrombus with the device so as to scrape the thrombus with the ribs.

32. The method of claim 31 wherein the device further provides for introduction of lytic drug into the thrombus through openings, or slits, created when the ribs are expanded.

33. The method of claim 31 and further including a concurrent addition of lytic drugs to the thrombus and scraping of the thrombus by the ribs.

34. The method of claim 31 and further including retracting the catheter from the thrombus by moving the mandril so as to linearly dispose the sleeve away from the ribs thereby causing the ribs to contract to a linear shape, and moving the device away from the thrombus.

35. The method of claim 31 and further including steps for:

providing a microcatheter;

positioning the device adjacent the microcatheter so that the device contains the thrombus and the microcatheter is adjacent to the thrombus; and delivering an additional volume of drugs through the microcatheter to the thrombus.

36. The method of claim 31 wherein the device provided further includes a handle in movable communication with the sleeve component so that pulling the mandril component while maintaining the handle stable produces a bowing of the ribs.

37. A method for macerating a thrombus in a living being, comprising:
providing a device that includes a main body that includes a sleeve, the sleeve positioned over coils wherein the sleeve and coils define a lumen; a core wire positioned within the lumen and attached to a distal end of the main body; and one or more strips positioned over the sleeve, the strips attached to the distal end and a proximal end segment;

pulling the core wire so as to push the coils together thereby bowing the strips in an outwardly direction; and positioning the device to contact a thrombus and contacting the thrombus with the device so as to scrape the thrombus with the strips.

38. The method of claim 37 wherein the device is prevented from twisting by the strips.

39. The method of claim 37 wherein the strips comprise wires.

* * * * *